United States Patent
Eyal et al.

(10) Patent No.: US 6,344,348 B1
(45) Date of Patent: Feb. 5, 2002

(54) PROCESS FOR THE PRODUCTION OF ASPARTIC ACID CONDENSATE

(75) Inventors: Aharon Eyal, Jerusalem (IL); Robert J. Jansen, Vilvoorde (BE); Asher Vitner, Jerusalem (IL); Pierre Cami, Languevoisin; Emmanuel Mailly, Les Ulis, both of (FR); Thomas Chattaway, Waterloo (BE); Bruno Jarry, Paris; Joelle More, Dourdan, both of (FR)

(73) Assignee: Amylum Belgium N.V., Aalst (BE)

( * ) Notice: Subject to any disclaimer, the term of this patent is extended or adjusted under 35 U.S.C. 154(b) by 0 days.

(21) Appl. No.: 09/284,234

(22) PCT Filed: Oct. 10, 1997

(86) PCT No.: PCT/GB97/02798

§ 371 Date: Nov. 22, 1999

§ 102(e) Date: Nov. 22, 1999

(87) PCT Pub. No.: WO98/16652

PCT Pub. Date: Apr. 23, 1998

(30) Foreign Application Priority Data

Oct. 13, 1996 (IL) .................................................. 119414

(51) Int. Cl.⁷ .............................. C12P 13/20; C12P 7/44
(52) U.S. Cl. ...................... 435/109; 562/552; 562/571; 435/142
(58) Field of Search ................................. 435/109, 142; 562/552, 571

(56) References Cited

U.S. PATENT DOCUMENTS 5,541,090 A * 7/1996 Sakano et al.

5,668,238 A * 9/1997 Yonek et al.

FOREIGN PATENT DOCUMENTS

| DE | 44 29 108 | 2/1996 |
| FR | 2 197 979 | 3/1974 |

OTHER PUBLICATIONS

Little et al., "Corrosion Inhibition by Thermal Polyaspartate", *American Chemical Society*, pp. 262–279, (1991).

Kokufuta et al., "Temperature Effect on the Molecular Weight and the Optical Purity of Anhydropolyaspartic Acid Prepared by Thermal Polycondensation", *Bulletin of the Chemical Society of Japan*, vol. 51(5), pp. 1555–1556, (1978).

* cited by examiner

*Primary Examiner*—Leon B. Lankford, Jr.
*Assistant Examiner*—Susan D. Coe
(74) *Attorney, Agent, or Firm*—Foley & Lardner

(57) ABSTRACT

The invention provides a process for the production of aspartic acid poly-condensate from a carbohydrate comprising the steps of: fermenting a carbohydrate-containing medium by means of a fumaric acid-producing microorganism, whereby a fumarate-containing fermentation liquor is formed; forming a purified ammonium fumarate solution from the fumarate-containing fermentation liquor; enzymatically converting the purified ammonium fumarate into purified ammonium aspartate; heating an aqueous solution of an aspartate salt derived from the purified ammonium aspartate whereby water is removed, an aspartic acid condensate is formed and a second product is formed, which second product is basic and contains the cation of the aspartate salt; and removing and using the basic second product as a reagent in another step of the process.

25 Claims, No Drawings

PROCESS FOR THE PRODUCTION OF ASPARTIC ACID CONDENSATE

The present invention relates to a process for the production of aspartic acid poly-condensates (herein also referred to as aspartic acid condensates). More particularly, the present invention relates to a process for the production of aspartic acid condensate from a carbohydrate via a fermentation route.

Aspartic acid is an acidic amino acid with a molecular formula of $HOOCCH_2CH(NH_3)COO$. It is used in products such as the aspartame sweetener and for formation of the biodegradable polymer polyaspartic acid (PAA). The latter could be utilized as a cobuilder or as a sequestrant in detergents, as a superabsorbent polymer and in other applications. The biodegradability of PAA is very attractive, and the potential market is large. It strongly depends, however, on the availability of a low cost aspartic acid and a non-contaminating process for the preparation of aspartic acid.

Heating of aspartic acid or compositions containing fumaric acid and/or maleic acid (or anhydride), and ammonia to temperatures of about 200° C. and higher, results in its polycondensation to polysuccinimide. The latter can be hydrolyzed to form polyaspartic acid or salts thereof. These products could be used in low phosphate environmentally-friendly detergent compositions. Presently these detergents contain polycarboxylic acids such as polyacrylic acid. These polycarboxylic acids have an important drawback, they are not biodegradable. Polyaspartic acid manufactured from aspartic acid is fully biodegradable (while that formed from fumaric acid, maleic acid or maleic anhydride is not). Yet, in order to replace the well established polycarboxylic acids, the polyaspartic acid should be compatible on price basis. This seems nearly impossible in the cost structure based on present technology.

In WO 93/23452 there is described and claimed a process for the preparation of a salt of polyaspartic acid comprising reacting maleic acid and ammonia, wherein the ammonia is present in molar excess at 200° C.–300° C., and converting the resultant polymer into a salt by adding a hydroxide.

In the publication, the following state of the prior art is noted:

U.S. Pat. No. 4,839,461 discloses a method for making polyaspartic acid from maleic acid and ammonia by reacting these constituents in a 1:1–1.5 molar ratio by raising the temperature to 120° C.–150° C. over a period of 4–6 hours and maintaining it for 0–2 hours.

U.S. Pat. No. 5,057,597 discloses a method for the polycondensation of aspartic acid to product polyaspartic acid by heating the aspartic acid in a fluidized bed reactor to 221° C. for a period of 3–6 hours in a nitrogen atmosphere followed by conventional alkaline hydrolysis.

Kovacs et al. (J. Org. Chem., 26 1084 [1961]) prepared polyaspartic acid by heating aspartic acid to 200° C. in a vacuo for a period of 120 hours, or in boiling tetralin over a period of 100 hours. Kovacs et al., showed that the intermediate formed in the thermal polymerization of aspartic acid was polysuccinimide.

In WO 95/00479 polyaspartic acid having a weight average molecular weight of 1000 to 5000 is produced by hydrolysis of anhydropolyaspartic acid that has been produced by condensation polymerization of L-aspartic acid, wherein conversion in excess of 80 percent is achievable utilizing "temperature vs. time" profiles.

In said publication, the following state of the prior art is noted:

Thermal condensation of aspartic acid to produce polyaspartic acid is taught by Etsuo Kokufuta, et al., "Temperature Effect on the Molecular Weight and the Optical Purity of Anhydropolyaspartic Acid Prepared by Thermal Polycondensation", Bulletin of the Chemical Society of Japan 51(5):1555–1556 (1978). Kokufuta et al. teach that the molecular weight of the polyaspartic acid produced by this method increases with increased reaction temperature. Moreover, the suggested maximum percent conversion of the aspartic acid to anhydropolyaspartic acid is no more than 68% using oil bath temperatures of between 163° C. (325° F.) and 218° C. (425° F).

A more recent work by Brenda J. Little et al., "Corrosion Inhibition By Thermal Polyaspartate" *Surface Reactive Peptides and Polymers*. pp 263–279, American Chemistry Society Symposium Series 444 (1990), cites Kokufuta et al. Oil bath temperatures of 190° C. (374° F.) were reportedly used to produce anhydropolyaspartic acid from powdered aspartic acid over a period of 24 to 96 hours. The reported results were no better than those reported by Kokufuta et al., however.

Presently, maleic anhydride is produced in a petrochemical process and isomerized to fumaric acid. Each mole of the latter is reacted with two moles of ammonia to form a solution of diammonium fumarate, which is converted in an enzymatic process (bioconverted) to monoammonium aspartate. The solution of monoammonium aspartate is reacted with a strong mineral acid, typically sulfuric acid. Protons are transferred from the strong acid to the aspartate ion to form aspartic acid. The solubility of aspartic acid in aqueous solutions is low and the acid is separated by crystallization. The ammonium salt of the strong mineral acid is formed as a low or negative value by-product.

Important contributors to the overall production costs are the consumption of the mineral acid and the losses of ammonia to the by-product. German patent 4,429,108 assigned to BASF suggests saving on the cost of mineral acid by heating ammonium aspartate or other derivatives of aspartic acid to form polysuccinimide. Thus, said patent teaches and claims a method for the polycondensation of ammonia derivatives of aspartic acid by heating asparagin, iso-asparagin, ammonium aspartate or aspartic acid diamide, characterized in that the polycondensation is performed at temperatures of at least 150° C. Thus, in the process of said application, the acidulation step is thereby avoided. Yet, the main cost element in the above described process is that of petrochemical fumaric acid. Fumaric acid was produced in the past by fermentation. A calcium base, probably calcium carbonate, was used as a neutralizing agent in the fermentation, which resulted in calcium fumarate. The fumaric acid was recovered from said salt by acidulation with sulfuric acid to form gypsum and fumaric acid. This method suffered from many difficulties. Some of them resulted from the fact that the neutralizing agent, calcium carbonate, the fermentation product, calcium fumarate, the final product, fumaric acid and the by-product, gypsum are all of low water solubility, which interferes in separation between reagents, products and by-product and between those and the biomass. Another problem results from the consumption of lime and sulfuric acid and the formation of gypsum to be disposed of. These and other important drawbacks, such as relatively low yield and low productivity in the fermentation, made the fermentation-produced fumaric acid more expensive than the petrochemical fumaric acid. The fermentation route was dropped in the forties. Based on this comparison one would not expect polyaspartic acid manufacture based on a fermentation-produced fumaric acid, using a carbohydrate as a raw material, to be competitive with polyaspartic acid based on petrochemical fumaric acid.

Furthermore, the fermentation route is fraught with problems relating to major impurities. In the petrochemical route fumaric acid is obtained in a quite pure form which, in turn, results in a relatively pure ammonium aspartate. In the fermentation route fumaric acid represents, according to prior art, only about 80% of the acids formed in the fermentation. Typically, glycerol, malic acid, succinic acid and ketoglutaric acid are also formed in the fermentation. In addition, the liquor formed in the fermentation contains nonutilized carbohydrates, mineral anions and cations resulting from the added nutrients, amino acids, proteins, biomass, etc. Considering the difficulties related to the low solubility of the reagents and the products in this fermentation as described above, one would expect most of these impurities to follow the fumarate into the bioconversion and to end-up in the ammonium aspartate. Many of them, particularly the carboxylic acids and the amino acids, are expected to block condensation of aspartic acid through chain termination and other mechanisms. That is particularly true in case acidulation of the ammonium aspartate solution and aspartic acid crystallization are avoided and ammonium aspartate is the feed material for the polycondensation.

It was surprisingly found that a salt of aspartic acid resulting from fermentation of a carbohydrate can be condensed by water removal without resorting to purifying it by acidulation and crystallization of aspartic acid. Thus, consumption of an acidulating acid and formation of undesired by-products are avoided. It was also found that the process forms, as a by-product, a basic compound which can be used as a reagent in another step of the process. The cost of reagents is thereby lowered. Furthermore, it was also surprisingly found that the formation of polyaspartic acid through he fermentation of a carbohydrate could be cheaper than starting from petrochemical fumaric acid.

A process for the production of aspartic acid polycondensate from a carbohydrate comprising the steps of:
a) fermenting a carbohydrate-containing medium by means of a fumaric acid-producing micro-organism, whereby a fumarate-containing fermentation liquor is formed, utilizing a base as a neutralizing agent of fumaric acid formed in said fermentation liquor, to form a fumarate salt;
b) forming a purified ammonium fumarate solution from said fumarate salt;
c) enzymatically converting said purified ammonium fumarate into purified ammonium aspartate with a molecular yield of 90–100% by treatment with an aspartase;
d) heating an aqueous solution of an aspartate salt derived from said purified ammonium aspartate whereby water is removed, an aspartic acid polycondensate is formed and a second product is formed, which second product is basic and contains the cation of said aspartate salt; and
e) removing and using said basic second product as a reagent in another step of the process.

Preferably said aspartic acid salt is selected from a group consisting of aspartates of ammonium, low molecular weight amine, alkali and alkaline earth metals. Most preferably said aspartate salt is ammonium aspartate. Preferably said second product is selected from a group consisting of ammonia, a low molecular weight amine and hydroxides, carbonates or bicarbonates of ammonium, low molecular weight amine, alkali and alkaline earth metals. Most preferably said second product is ammonia.

In preferred embodiments of the present invention the aspartic acid moiety of said condensate is mainly in its L-form.

A carbohydrate is used as a raw material for producing said aspartate salt. In the first step a carbohydrate-containing medium is fermented by a fumaric acid-producing micro-organism. Said fermentation of carbohydrate is typically using microorganisms belonging to the order Mucorales, especially *Rhizopus arrhizus, Rhizopus oryzac, Rhizopus nigricans* or other related genera. Other microorganisms like Candida may be used alternately. The fermentation medium can contain, in addition to the carbohydrate, nutrients such a nitrogen source and minerals. Suitable nitrogen sources include such organic and inorganic sources as urea, ammonium chloride, ammonium sulfate, ammonium acetate, ammonium nitrate, ammonium biphosphate, asparagin and protein hydrolysates. Of the foregoing, urea and ammonium sulfate are preferred. The inorganic salts added to the culture media should include sources of phosphate, sulfur, iron magnesium and zinc. Suitable sources of phosphate include monobasic or dibasic sodium phosphate, monobasic or dibasic potassium phosphate, ammonium biphosphate, or mixtures thereof. Suitable inorganic salts employed in the fermentation include zinc sulfate, iron salts such as ferric tartrate or ferric chloride, and magnesium sulfate. Corn steep liquor or biotin may be added for vitamin supply. The fermentation is conducted at a temperature of about 25° C. to about 35° C., preferably at about 33° C. to about 35° C. Fungi can grow satisfactorily in acidic conditions. However, as the build-up of fumaric acid in the fermentation medium has a negative effect on the fermentation, the latter is typically conducted at a slightly acidic pH, from about 4 to 7. Typically a base is directly added as a neutralizing agent and a fumarate salt is formed. Usually the neutral salt of fumaric acid is formed rather than the acidic salt. Said neutralizing agent can be selected from a group consisting of ammonia and hydroxides, carbonates or bicarbonates of ammonium, alkali and alkaline earth metals. Most preferably calcium carbonate is used as a neutralizing agent and calcium fumarate is formed.

In preferred embodiments of the present invention, the carbohydrate is selected from the group consisting of dextrose, preferably produced from cereal starch, including low-grade wheat starch fractions and molasses.

Alternatively, the fumaric acid is continuously removed from the fermentation medium, e.g. by binding to a water immiscible liquid or solid basic extractant or adsorbent. For that purpose one can use a basic extractant, e.g. of the type containing a long chain amine, or a basic resin such as the anion exchangers that carry non-quarternary amine functions or pyridine based resins. The fumaric acid can be recovered from said extractant or adsorbent by contacting with a basic solution which consumes a base and forms the fumarate salt. This use of a base will further be referred to as indirect neutralization, it being realized that a base can be used directly or indirectly as a neutralizing agent in said fermentation. The base for that purpose is preferably selected from the group consisting of ammonia and hydroxides, carbonates and bicarbonates of ammonium, alkali and alkaline earth metals. Most preferably this base is ammonia.

Ammonium fumarate is enzymatically converted to ammonium aspartate. Usually the conversion is conducted in a slightly basic medium so that diammonium fumarate is the substrate. Ammonium fumarate formed in fermentation could be fed to said enzymatic conversion. (As used herein, if not defined specifically, the term ammonium fumarate is intended to denote monoammonium fumarate, diammonium fumarate, or a combination thereof). In those cases where the fermentation results in another fumarate salt, as in the case of the preferred embodiment where calcium carbonate is the neutralizing agent and calcium fumarate is the product, this salt is converted to ammonium fumarate. This is preferably effected by a direct or an indirect reaction with ammonia, ammonium carbonate or ammonium bicarbonate.

A most preferred embodiment is described in Israel specification 116,849. Precipitated calcium fumarate formed in the fermentation is separated from the fermentation liquor, washed, suspended in water or in an aqueous solution from a previous step and dissolved at an elevated temperature. The calcium fumarate solution can be purified, if needed, by methods such as membrane filtration, ion-exchange, active carbon treatment, solvent extraction, etc. Then it is preferably recrystallized. After recrystallization it is reacted with ammonia and $CO_2$ or with ammonium carbonate of bicarbonate. Preferably the pH in the reaction medium is first adjusted to between about 10 and 11. High temperatures and high $CO_2$ pressures are not required. In the reaction, calcium fumarate is converted to ammonium fumarate. The amount of water in the reaction is adjusted so that the ammonium fumarate formed will be quite concentrated, preferably greater than 10% and even more preferred higher than 13%. Calcium carbonate is formed as a by-product, separated from the ammonium fumarate solution and reused as a neutralizing agent, in carbohydrates fermentation to fumaric acid. Preferably the calcium carbonate is calcined prior to the recycle to fermentation, whereby biomass left in it is removed. In a most preferred embodiment the calcined calcium base is quenched in water and kept suspended in the water until reused. This suspension in water helps in removing ashes left from biomass burning and other ashes left from the previous fermentation step.

In a preferred embodiment the ammonium fumarate directly formed in the fermentation or indirectly through conversion of another fumarate salt formed in the fermentation, is purified prior to the enzymatic conversion to ammonium aspartate. Purification can be conducted in known methods such as recrystallization, membrane filtration, ion-exchange, active carbon treatment, solvent extraction, etc. In a preferred embodiment an aqueous solution containing diammonium fumarate, resulting from fermentation, is contacted with a cation exchanger, which is at least partially in its acid form, whereby ammonium ions are adsorbed on said cation exchanger and part of said diammonium fumarate is converted to monoammonium fumarate. The aqueous solution is then separated from said ammonium ion-carrying cation exchanger and monoammonium fumarate is separated from said solution. In a preferred embodiment this solution is recontacted with a cation exchanger which is in at least partially acidic form. Said separation, which provides for purification, can be affected in various known ways. A preferred separation method is through crystallization. Said purified monoammonium fumarate, optionally after further purification, is converted back to diammonium fumarate and used as a precursor in the enzymatic conversion to ammonium aspartate. In a preferred embodiment said monoammonium fumarate is contacted with said ammonium ion-carrying cation exchanger, whereby said cation exchanger is converted to its at least partially acid form for reuse in the process. The monoammonium fumarate is converted to diammonium fumarate, which is used as a precursor in the enzymatic conversion to ammonium aspartate.

Thus, in an especially preferred embodiment, the process of the present invention comprises the additional steps of (i) contacting an aqueous solution containing diammonium fumarate resulting from said fermentation with a cation exchanger which is at least partially in its acid form, whereby ammonium ions are adsorbed on said cation exchanger and part of said diammonium fumarate is converted to monoammonium fumarate; (ii) separating the aqueous solution from said ammonium ion-carrying cation exchanger; and (iii) separating monoammonium fumarate from said solution, converting the same to diammonium fumarate and using said diammonium fumarate in the enzymatic conversion to ammonium aspartate.

As stated, the ammonium fumarate is converted to ammonium aspartate in an enzymatically catalyzed reaction. Typically, most of the ammonium aspartate is monoammonium aspartate, but a small fraction could be in diammonium aspartate form. The term ammonium aspartate as used herein is intended to denote both monoammonium aspartate and its mixtures with diammonium aspartate, unless otherwise indicated.

The enzymatic reaction is catalysed by the enzyme aspartate. This enzyme can be produced from many microorganism, including *E coli*, Brevibacterium sp, Pseudomonas sp. cultivated in a suitable medium. The ammonium aspartate formation can be obtained by contacting the ammonium fumarate solution directly with the bacterial culture or with permeabilized cells, crude cell extracts, or purified aspartase. When bacterial culture is used directly, the method described in French Patent Publication No. 2,197,979 (1972) can be employed. Cell culture, cells, cell extracts or enzyme itself can be used directly or as immobilized preparations. Examples of immobilized preparations are obtained by immobilizing the cells, cell extracts or enzyme on supports, carriers or bases such as polyacrylamide gels, sulfur-containing polysaccharide (e.g. carrageenan, furcellaran, etc.), gel, collagen gel, alginic acid gel, polyvinyl alcohol gel, agar gel, resins and the like.

The ammonium fumarate concentration in the feed to the conversion is typically from about 0.5M to about 2M. It is usually preferable to add a divalent metal ion such as calcium ion, magnesium ion, manganese ion, strontium ion or the like to the reaction system to improve the enzyme stability. The amount of the divalent ion can be about 0.1 to 10 mM. The reaction is conducted at temperatures of from about 20° C. to 60° C., and the pH is preferably between 7 to 9. The yield of conversion is typically 90% to 100%.

The aspartate formed can be fed to the condensation step as ammonium aspartate, or converted to another aspartate salt such as that of low molecular weight amine, alkali and alkaline earth metals. The conversion is conducted by reaction with the corresponding base (hydroxide, carbonate or bicarbonate). Preferably the ammonium based by-product formed in such conversion (selected from a group consisting of ammonia, ammonium carbonate and ammonium bicarbonate) is separated and reused. In the case of ammonia, a preferred way of separation is distillation simultaneously with or after the reaction. Ammonium bicarbonate could be separated by crystallization. The ammonium base can be used directly or indirectly as a neutralizing agent in the fermentation, or for converting another fumarate salt formed in the fermentation to ammonium fumarate.

In the condensation step an aqueous solution of an aspartate salt derived from ammonium aspartate is heated whereby water is removed. The water to be removed is the water entering the reaction as the solvent for the aspartate salt, as well as water formed in the condensation, one or two molecules of water per molecule of aspartate salt. While part of the water can be removed by adsorption, e.g. on a suitable molecular sieve, or through binding to a hydrophilic compound, e.g. calcium chloride or sulfuric acid, at least the last portion of it will have to be removed at an elevated temperature into the vapor phase. Pulling vacuum on the solution or driving a carrier gas through it assist in said removal of water. In a preferred embodiment said carrier gas is $CO_2$. In another preferred embodiment the aqueous solution of the aspartate salt is first concentrated to above 70% dry solid and then heated in a pressure vessel.

When the aspartate salt is ammonium or a low molecular weight amine aspartate, ammonia or low molecular weight amine, the basic second product, follows water into the vapor phase from which it can be recovered. The recovered ammonia can be reused for direct or indirect neutralization of the fermentation medium and ammonia and low molecular weight amine can be used for converting another fumarate salt formed in the fermentation to ammonium fumarate. In case the aspartate salt is that of alkali or alkaline earth metals, bases of these cations could be formed as basic second products and separated from the reaction mixture, e.g. by crystallization. In cases where $CO_2$ is used as a carrier gas, those bases could be carbonates or bicarbonates. The alkali or alkaline earth metal bases can be reused as neutralizing agents in fumaric acid fermentation. Furthermore, said bases and the low molecular weight amine can be used for conversion of ammonium aspartate to the desired aspartate salt.

Thus, in a first preferred embodiment of the present invention said second basic product is used as a neutralizing agent in fermentation step a of the process. In a second preferred embodiment of the present invention said second basic product is selected from ammonia and low-molecular weight amine and used to convert fumarate salts other than ammonium fumarate formed in step a, e.g. calcium fumarate, to ammonium fumarate. In a third preferred embodiment of the present invention said second basic product is selected from low molecular weight amine, and hydroxides, carbonates and bicarbonates of ammonium, alkali and alkaline earth metals and used for conversion of ammonium aspartate formed in step c into an aspartate salt used in step d.

The rate of water and ammonia removal and that of the precipitation of the basic salts, as well as the rate of condensation, are determined by the conditions in the heating step, including the temperature, the rate of carrier gas transfer and the nature of said carrier gas.

The temperature of the reaction mixture is first determined by the partial vapor pressure of the water in the solution. In an atmospheric pressure the temperature will increase slowly from about 100° C. There is a possibility of adding some water to the reaction mixture from time to time to control its temperature and to assist in ammonia removal. Steam can be used for both heat supply and as a carrier gas. The maximal temperature of the reaction medium should be at least 130° C. and preferably at least 180° C.

Various reactors could be used for the heating step, including extruders, mixers and a variety of dryers such as plate, belt and screw dryers. In a preferred embodiment the heating is effected in a heat exchanger, equipped, preferably full length, with a static mixer in each tube, e.g. in a heat exchanger such as the Kenics Heat Exchanger® equipped with streamlined Kenics Static Mixer® elements in each heat exchanger tube.

A catalyst can be used in the reaction. Acids and acidic salts were found suitable. It is important not to add an acid or an acidic salt to the aqueous solution of the aspartate salt fed to the heating step as this will be equivalent to adding an acidulating agent in the reaction and would result in the formation of a by-product salt. Addition of an acid or acidic catalyst therefore is carried out in step d after most, e.g. at least 75% and preferably 85%, of the basic second product is removed.

Suitable catalysts are selected from a group comprising mineral acids, particularly phosphoric acid, acidic salt, fumaric acid and monoammonium fumarate. Preferably the catalyst is separated from the reaction and reused. For example, such separation could be by washing from water-insoluble products such as polysuccinimide or by membrane separation from water-soluble polymeric products such as polyaspartic acid and salts thereof.

Fumaric acid to be used as a catalyst could be formed by disproportionation of monoammonium fumarate, formed, e.g. by the above-described cation exchange treatment, into fumaric acid and diammonium fumarate. Such disproportionation could be effected by contact with relatively weak base extractants or adsorbents. Those extractant or adsorbents are preferably of pKa of less than 5 and more preferably less than 4. Recovery of the fumaric acid bound to extractant or adsorbent is preferably by washing with water at elevated temperature.

The walls of the reactor could reach temperatures of 200° C. and higher. Direct contact between those and the formed condensation product is preferably avoided. This could be achieved by the presence of a solvent. By selecting solvents of right properties the solvent could have some additional functions. Solvents that form an azeotrop with water, e.g. butanol, assist in water removal into the vapor phase. For that purpose the boiling point of the azeotrop is preferably lower than that of the maximal reaction mixture. The solvent can dissolve and thereby remove some impurities. Other solvents can dissolve the formed condensate and thereby facilitate the condensation and separation thereof from impurities. In a preferred embodiment the solvent is an alkanol that can form intermediate products with the aspartate, such as esters. Those can help in the removal of the basic second product and provide a condensed product (from which water is already removed), to the next step of aspartic acid condensation.

In a preferred embodiment the condensate of aspartic acid formed in the heating step is selected from a group consisting of aspartic acid esters, polysuccinimide, polyaspartic acid and salts thereof.

Polysuccinimide can be converted to polyaspartic acid or salts thereof by hydrolysis. More specifically, the potassium salt of polyaspartic acid is formed on reacting the polysuccinimide with an aqueous solution of KOH, preferably in warm solution. Polysuccinimide is not soluble in water, while the polyaspartate salts are highly soluble. This provides an additional tool for purification of the product. In the cases where the polysuccinimide is obtained in a solvent solution, the hydrolysis transfers it into the aqueous solution, resulting in even higher purity.

The condensate, particularly polysuccinimide, could get some coloring during the heating step. Part of the color in the polysuccinimide could follow to the polyaspartic acid and salts thereof formed on hydrolysis. Bleaching by oxidizing chemicals was proposed. Such bleaching, using undesired reagents, could cause waste management difficulties and may damage the product. It should therefore minimized and, if possible, avoided. It was found that careful control of the overheating, particularly by the use of the preferred reactor and in the presence of a solvent, reduces very significantly the color formation. Color could be removed by adsorbing resins and active materials. Other purification means, such as membrane filtration, ion exchange and solvent extraction can be used particularly on aqueous solutions of condensates such as polyaspartic acid and salts thereof.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE

A 10 liter sterile solution containing 1270 g dextrose, 17.5 g $(NH_4)_2SO_4$, 4 g $MgSO_4.7 H_2O$, 3 g $KH_2PO_4$, 0.5 g $ZnSO_4.7H_2O$, 0.1 g $FeCl_3.6 H_2O$, 5 g corn steep liquor and 960 g of $CaCO_3$ in suspension is fermented at 34° C. using *Rhizopus arrhizus* strain NRRL 1526.

After 54 hours of fermentation 800 g of fumaric acid is produced as calcium salt.

The broth is filtered to get a cake of the mycclium and calcium fumarate which is washed with 2 liters of cold water. The washed cake contains 720 g of fumaric acid as its calcium salt. The cake is suspended in 12 liters of boiling water with agitation for one hour and then filtered at 95° C. to obtain a calcium fumarate solution. Calcium fumarate is crystallized by cooling the filtrate at 10° C. for 2 hours. The calcium fumarate is filtered, washed in 1 liter of cold water and dried to obtain 850 g of calcium fumarate, with a purity higher than 90%. 790 g of this calcium fumarate is suspended in 4.5 liters of 180 g ammonia water solution and $CO_2$ is bubbled until the pH reaches 9.5. Calcium carbonate precipitate is filtered and washed in cold water. 4.5 liters of diammonium fumarate solution containing 540 g of fumaric acid is obtained.

This solution, heated at 75° C., is percolated in a 5 liter cation exchange column. The column is washed with 3 liters of water. This column is named column A. 5 liters of the effluent containing 500 g of fumaric acid, mainly as monoammonium fumarate, is concentrated under reduced pressure at 70° C. to obtain 2 liters of concentrate.

After cooling for 2 hours at 10° C., monoammonium furrarate crystalizes with a 99% purity.

The crystals are separated by filtration and dissolved in water at 75° C., the solution is percolated on a 2-liter column B fed with resin taken out of column A after percolation of the diammonium fumarate solution. The column B is then washed with water.

The result is 1.5 liter of solution containing 180 g of fumaric acid as its diammonium salt.

This solution, using the bacterium Pseudomonas fluorescens strain ATCC21973 at 58° C., is converted from diammonium fumarate to ammonium aspartate in 35 hours with a molecular yield higher than 95%.

150 g of pure N decanol is first put into a four-neck 500 ml baloon heated by an oil thermo-regulated bath, one neck for agitation, one for temperature measurement. one for reactant adding and the the last for gas recovery connected to a water condenser, followed by a 2 liter externally cooled receptor with water.

The decanol is heated at 150° C. and maintained at this temperature by the thermo-regulation as 800 ml of the ammonium aspartate solution (150 g of aspartic acid) is drip-fed to the reactor for a period of 3 hours, and also decanol is added to keep a constant reaction volume.

During this period of time water and ammonia are continuously removed out of the reactant medium and at the end of the addition the temperature regulation is set at 210° C.

Water azeotropic distillation starts at 180° C. as the suspended solid in the reactant medium turns to a pink color.

After 30 minutes temperature regulation is set at 230° C.

Water azeotropic distillation continues as the color turns from pink to orange-pink.

After 30 minutes the heating bath is removed and the reactant medium cooled down to 90° C. in 1 hour while under constant agitation.

The reactant medium is then filtered and the cake washed 5 times with 100 ml of absolute alcohol, which washing removes some coloration in the filtrate. The cake is dried at 40° C. under vacuum to get 95 g of orange-pink fine powder.

Analysis of ammonia nitrogen in the receptor shows that more than 96% of the ammonia initially present in the aspartate solution is removed and that nearly 2 moles of water are produced during the polycondensation reaction.

50 g of the solid is suspended in 50 g of water at 40° C. and a stiochiometric amount of 50% KOH solution is drip-added so that the pH stays under 10.

The polysuccinimide dissolves to form the potassium salt of alpha-beta-polyaspartic acid.

Total nitrogen and amino nitrogen are measured, the ratio total nitrogen on amino nitrogen is found to be equal to 165, which means a 20,000 Dalton molecular weight for polyaspartic acid.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as ilustrative and not restrictive, reference being made to the appended claims. rather than to the foregoing description, and all changes which come within the meaning and range of equivalency of the claims are therefore intended to be embraced therein.

What is claimed is:

1. A process for the production of aspartic acid polycondensate from a carbohydrate, comprising:

(a) fermenting a carbohydrate-containing medium that also contains a base, by using a fumaric acid-producing micro-organism, whereby a fumarate-containing fermentation liquor is formed;

(b) converting the fumarate in the fermentation liquor into purified ammonium fumarate;

(c) enzymatically converting said purified ammonium fumarate into ammonium aspartate with a yield of conversion of 90–100% by treatment with an aspartase;

(d) heating an aqueous solution of said ammonium aspartate, at least a portion of which may be in the form of another aspartate salt formed from said ammonium aspartate, whereby water is removed, an aspartic acid poly-condensate is formed, and a second product is formed, wherein the second product is basic and contains the cation of said other aspartate salt or ammonium aspartate; and (e) removing and using said basic second product as a reagent upstream in the process.

2. A process according to claim 1, wherein the aspartic acid moiety of said poly-condensate is mainly in its L-form.

3. A process according to claim 1, wherein said base used in (a) is selected from the group consisting of ammonia and hydroxides, carbonates and bicarbonates of ammonium, alkali and alkaline earth metals.

4. A process according to claim 1, wherein said base used in (a) is ammonia.

5. A process according to claim 3, wherein said hydroxides, carbonates or bicarbonates are salts of alkaline earth metals, whereby alkaline earth metal fumarate salts are formed.

6. A process according to claim 5, wherein said alkaline earth metal fumarate salts are converted into a purified ammonium fumarate.

7. A process according to claim 1, wherein said other aspartate salt is selected from the group consisting of aspartates of low molecular weight amines, alkali or alkaline earth metals.

8. A process according to claim 1, wherein said aspartic acid poly-condensate formed in (d) is selected from the group consisting of aspartic acid esters, polysuccinimide, polyaspartic acid and salts thereof.

9. A process according to claim 1, wherein said second basic product containing the cation of said other aspartate salt or ammonium aspartate is selected from the group consisting of ammonia, low molecular weight amines, and hydroxides, carbonates and bicarbonates of ammonium, alkali and alkaline earth metals.

10. A process according to claim 9, wherein said second basic product is used as a neutralizing agent in (a).

11. A process according to claim 9, wherein said second basic product is selected from ammonia and low-molecular weight amines and used to convert fumarate salts other than ammonium fumarate formed in (a) to ammonium fumarate.

12. A process according to claim 9, wherein said second basic product is selected from low molecular weight amines, and hydroxides, carbonates and bicarbonates of ammonium, alkali and alkaline earth metals and used for conversion of ammonium aspartate formed in (c) into another aspartate salt used in (d).

13. A process according to claim 1, further comprising:
(i) contacting an aqueous solution containing diammonium fumarate resulting from (b) with a cation exchanger, which is at least partially in its acid form, whereby ammonium ions are adsorbed on said cation exchanger and at least a part of said diammonium fumarate is converted to monoammonium fumarate;
(ii) separating the aqueous solution from said ammonium carrying cation exchanger; and
(iii) separating monoammonium fumarate from said solution, wherein said monoammonium fumarate is purified, converting the same to diammonium fumarate and using said diammonium fumarate in (c), the enzymatic conversion to ammonium aspartate.

14. A process according to claim 13, wherein said monoammonium fumarate is contacted with said ammonium ion carrying cation exchanger, whereby said cation exchanger is converted to an at least partially acid form and monoammonium fumarate is converted to diammonium fumarate.

15. A process according to claim 14, wherein said converted cation exchanger is reused to convert diammonium fumarate to monoammonium furmarate.

16. A process according to claim 1, wherein said aspartic acid poly-condensate is selected from the group consisting of polyaspartic acid and its salts.

17. A process according to claim 1, wherein in (d), ammonia is evolved during heating, collected from the vapor phase and reused upstream in the process.

18. A process according to claim 1, comprising adding an acidic catalyst in (d) after removing at least 75% of the basic second product.

19. A process according to claim 1, wherein a gas is driven through the heated solution of (d).

20. A process according to claim 19, wherein said gas is $CO_2$.

21. A process according to claim 1, wherein said carbohydrate is selected from the group consisting of dextrose and molasses.

22. A process according to claim 1, wherein the heating of (d) is effected in a multi-tube heat exchanger equipped with static mixers in each tube.

23. A process according to claim 1, wherein the heating of (d) is effected in the presence of an alkanol solvent.

24. A process according to claim 1, wherein said other aspartate salt is selected from the group consisting of aspartates of amines, alkali or alkaline earth metals.

25. A process according to claim 1, wherein said other aspartate salt is selected from the group consisting of aspartates of alkali or akaline earth metals.

* * * * *